(12) United States Patent
Kiesslich et al.

(10) Patent No.: US 8,742,189 B2
(45) Date of Patent: Jun. 3, 2014

(54) CATALYST FOR THE DEHYDROAROMATISATION OF METHANE AND MIXTURES CONTAINING METHANE

(75) Inventors: Frank Kiesslich, Dietzenbach (DE); Joana Coelho Tsou, Heidelberg (DE); Bilge Yilmaz, Mannheim (DE); Sebastian Ahrens, Wiesloch (DE); Thomas Heidemann, Viernheim (DE); Veronika Will, Graben-Neudorf (DE); Christian Bechtold, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 657 days.

(21) Appl. No.: 12/937,062

(22) PCT Filed: Apr. 8, 2009

(86) PCT No.: PCT/EP2009/054201
§ 371 (c)(1),
(2), (4) Date: Jan. 26, 2011

(87) PCT Pub. No.: WO2009/124960
PCT Pub. Date: Oct. 15, 2009

(65) Prior Publication Data
US 2011/0124933 A1    May 26, 2011

(30) Foreign Application Priority Data

Apr. 8, 2008   (EP) .................................... 08154195
Dec. 18, 2008  (EP) .................................... 08172159

(51) Int. Cl.
*C07C 15/00* (2006.01)
*C07C 15/04* (2006.01)
*B01J 29/06* (2006.01)

(52) U.S. Cl.
USPC ............. 585/417; 585/407; 585/415; 502/60; 502/61; 502/62; 502/63; 502/64; 502/66; 502/71; 502/73; 502/74; 502/77

(58) Field of Classification Search
USPC ........... 502/60, 61, 62, 63, 64, 66, 71, 73, 74, 502/77; 585/407, 415, 417
See application file for complete search history.

(56) References Cited

FOREIGN PATENT DOCUMENTS

| EP | 0 036 707 | 9/1981 |
|----|-----------|--------|
| WO | 2005 032713 | 4/2005 |
| WO | 2009 124902 | 10/2009 |
| WO | 2010 076251 | 7/2010 |

OTHER PUBLICATIONS

Dong et al., Studies on Mo/HZSM-5 complex catalyst for methane aromatization, 2004, Journal of Natural Gas Chemistry vol. 13, 36-40.*

U.S. Appl. No. 13/142,718, filed Jun. 29, 2011, Coelho Tsou, et al.
U.S. Appl. No. 13/186,592, filed Jul. 20, 2011, Schneider, et al.
U.S. Appl. No. 31/202,427, filed Aug. 19, 2011, Coelho Tsou, et al.
U.S. Appl. No. 13/259,863, filed Sep. 23, 2011, Coelho Tsou, et al.
U.S. Appl. No. 13/260,053, filed Sep. 23, 2011, Coelho Tsou, et al.
U.S. Appl. No. 13/256,536, filed Sep. 14, 2011, Tsou, et al.
Li, S., et al., "The function of Cu(II) ions in the Mo/CuH-ZSM-5 catalyst for methane conversion under non-oxidative condition," Applied Catalysis A: General, vol. 187, pp. 199-206, (1999).
Song, Y., et al., "Hydrothermal post-synthesis of HZSM-5 zeolite to enhance the coke-resistance of Mo/HZSM-5 catalyst for methane dehydroaromatization," Catalysis Letters, vol. 109, Nos. 1-2, pp. 21-24, (Jun. 2006).
Li, Y., et al., "Enhanced performance of methane dehydro-aromatization on Mo-based HZSM-5 zeolite pretreated by $NH_4F$," Catalysis Communications, vol. 8, pp. 1567-1572, (2007).
Dong, Q., et al., "Studies on Mo/HZSM-5 Complex Catalyst for Methane Aromatization," Journal of Natural Gas Chemistry, vol. 13, No. 1, pp. 36-40, (2004).
Wang, D., et al., "Characterization of a Mo/ZSM-5 Catalyst for the Conversion of Methane to Benzene," Journal of Catalysis, vol. 169, Article No. CA971712, pp. 347-358, (1997).
Wang, L., et al., "Activity and stability enhancement of Mo/HZSM-5-based catalyst for methane non-oxidative transformation to aromatics and $C_2$ hydrocarbons: Effect of additives and pretreatment conditions," Applied Catalysis A: General, vol. 152, pp. 173-182, (1997).
Zhang, Y., et al., "Influence of Pretreatment Conditions on Methane Aromatization Performance of Mo/HZSM-5 and Mo-Cu/HZSM-5 Catalysts," Journal of Natural Gas Chemistry, vol. 12, No. 2, pp. 145-149, (2003).
Xu, Y., et al., "Direct conversion of methane under nonoxidative conditions," Journal of Catalysis, vol. 216, pp. 386-395, (2003).
Qi, S., et al., "Methane aromatization using Mo-based catalysts prepared by microwave heating," Catalysis Today, vol. 98, pp. 639-645, (2004).
Weckhuysen, B.M., et al., "Conversion of Methane to Benzene over Transition Metal Ion ZSM-5 Zeolites," Journal of Catalysis, vol. 175, Article No. CA982010, pp. 338-346, (1998).
Weckhuysen, B.M., et al., "Characterization of surface carbon formed during the conversion of methane to benzene over Mo/H-ZSM-5 catalysts," Catalysis Letters, vol. 52, pp. 31-36, (1998).
International Search Report issued Jul. 23, 2009 in PCT/EP09/054201 filed Apr. 8, 2009.

(Continued)

*Primary Examiner* — Elizabeth Wood
(74) *Attorney, Agent, or Firm* — Oblon, Spivak, McClelland, Maier & Neustadt, L.L.P.

(57) ABSTRACT

The present invention relates to a catalyst for dehydroaromatizing $C_1$-$C_4$-aliphatics, said catalyst being obtainable by twice treating a zeolite from the group of MFI and MWW with $NH_4$-containing mixtures, in each case with subsequent drying and calcination. The catalyst comprises molybdenum and, if appropriate, as further elements, Cu, Ni, Fe, Co, Mn, Cr, Nb, Ta, Zr, V, Zn and/or Ga.

The present invention further provides a process for dehydroaromatizing a mixture comprising $C_1$-$C_4$-aliphatics by conversion in the presence of the catalyst.

27 Claims, No Drawings

(56) References Cited

OTHER PUBLICATIONS

U.S. Appl. No. 12/937,144, filed Nov. 23, 2010, Kiesslich, et al.
U.S. Appl. No. 12/993,956, filed Nov. 22, 2010, Kiesslich, et al.
Wang, L. et al., "Activity and Stability Enhancement of Mo/HZSM-5-Based Catalysts for Methane Non-Oxidative Transformation to Aromatics and $C_2$ Hydrocarbons: Effect of Additives and Pretreatment Conditions" Applied Catalysis A: General, vol. 152, No. 2, pp. 173-182 (May 7, 1997) XP-004338065.
Ohnishi, R. et al., "Catalytic Dehydrocondensation of Methane With CO and $CO_2$ Toward Benzene and Naphthalene on Mo/HZSM-5 and Fe/Co-Modified Mo/HZSM-5" Journal of Catalysis, vol. 182, No. 1, pp. 92-103 (Feb. 15, 1999) XP-004443221.
International Preliminary Report on Patentability Issued on Jul. 22, 2010 in PCT/EP09/054201 filed Apr. 8, 2009.
U.S. Appl. No. 13/128,895, filed May 12, 2011, Heidemann, et al.
U.S. Appl. No. 13/393,837, filed Mar. 2, 2012, Schneider, et al.
U.S. Appl. No. 13/500,966, filed Apr. 9, 2012, Tsou, et al.
U.S. Appl. No. 13/383,014, filed Jan. 9, 2012, Kubanek, et el.
U.S. Appl. No. 13/383,321, filed Jan. 10, 2012, Kubanek, et el.

\* cited by examiner

1

CATALYST FOR THE DEHYDROAROMATISATION OF METHANE AND MIXTURES CONTAINING METHANE

CROSS REFERENCE TO RELATED APPLICATIONS

The present application is a 35 U.S.C. §371 national stage patent application of International patent application PCT/EP09/054,201, filed on Apr. 8, 2009, the text of which is incorporated by reference, and claims the benefit of the filing date of European application nos. EP08154195.5, filed on Apr. 8, 2008 and EP08172159.9, filed on Dec. 18, 2008, the text of each also being incorporated by reference.

The present invention relates to a catalyst for dehydroaromatizing $C_1$-$C_4$-aliphatics, said catalyst being obtainable by twice treating a zeolite from the group of MFI and MWW with $NH_4$-containing mixtures, in each case with subsequent drying and calcination. The catalyst comprises molybdenum and, if appropriate, as further elements, Mn, Cr, Nb, Ta, Zr, V, Zn, Ga, Cu, Ni, Fe and/or Co.

The present invention further provides a process for dehydroaromatizing a mixture comprising $C_1$-$C_4$-aliphatics by conversion in the presence of the catalyst.

Aromatic hydrocarbons such as benzene, toluene, ethylbenzene, styrene, xylene and naphthalene are important intermediates in the chemical industry, the demand for which continues to rise. In general, they are obtained by catalytic reformation from naphtha which in turn is obtained from mineral oil. Recent studies show that global mineral oil reserves are more limited compared with natural gas reserves. Therefore, the preparation of aromatic hydrocarbons from reactants which can be obtained from natural gas has become an alternative of economic interest. The main component of natural gas is typically methane.

One possible reaction route to obtaining aromatics from aliphatics is nonoxidative dehydroaromatization (DHAM). The reaction is effected under nonoxidative conditions, more particularly with exclusion of oxygen. In DHAM, dehydrogenation and cyclization of the aliphatics take place to give the corresponding aromatics with release of hydrogen.

For catalysis of nonoxidative dehydroaromatization, H-ZSM-5 zeolites modified with molybdenum have been found to be particularly suitable.

D. Wang et al. describe (Journal of Catalysis 169, (1997), pages 347 to 358) the nonoxidative conversion of methane to benzene over H-ZSM-5 catalysts which comprise 2% by weight of molybdenum. Methane conversions between 4 and 8% coupled with benzene selectivities of approx. 60% were achieved.

L. Wang et al. (Applied Catalysis A: General 152, (1997), pages 173 to 182) conducted the nonoxidative dehydroaromatization over molybdenum-containing H-ZSM-5 catalysts and studied the influence of different pretreatment methods and the doping of the catalyst with further metals. The methane conversions were between 3 and 5% at selectivities for benzene and toluene of up to 96%. Doping with lanthanum and vanadium did not exhibit any positive effect; doping with tungsten or zirconium was found to be advantageous.

Y. Zhang et al. (Journal of Natural Gas Chemistry 12, (2003), pages 145 to 149) studied the influence of the pretreatment of Mo/H-ZSM-5 which had been used doped with copper and undoped on the hydroaromatization of methane. The presence of copper enhanced the methane conversion significantly from 7.5 to 10.5% by weight with equal benzene selectivity.

Y. Xu et al. (Journal of Catalysis 216, (2003), pages 386 to 395) describe, in a review article, the problems which occur when molybdenum-containing H-ZSM-5 catalysts are used for the dehydroaromatization of methane. More particularly, the deactivation of the catalyst by coke deposits constitutes a great problem. Y. Xu et al. summarize some of the means described in the literature for improving the activity and stability of Mo/H-ZSM-5 catalysts, such as steam dealumination, dealumination by acidic solutions or silanization.

S. Qi and W. Yang (Catalysis Today 98, (2004), pages 639 to 645) report that the methane conversion and the benzene selectivity over an Mo/H-ZSM-5 zeolite catalyst can be increased by measures including addition of copper. For instance, the conversion of methane rises from 18 to 20% at benzene selectivities of up to about 95%. The doping additionally has a positive influence on the stability and the coking tendency of the catalyst.

S. Li et al. (Applied Catalysis A: General 187, (1999), pages 199 to 206) studied the nonoxidative dehydroaromatization of methane over copper-doped Mo/H-ZSM-5 catalysts in comparison to the undoped catalysts. Commercially available H-ZSM-5 zeolite was calcined and boiled in water, and an ion exchange was carried out with ammonium nitrate. Subsequently, the zeolite was dried and calcined. In the case of the copper-doped zeolite, the copper$^{2+}$ ions were likewise applied by means of ion exchange. The zeolite pretreated in this way was subsequently mixed mechanically with the appropriate amount of molybdenum oxide and calcined. As a result of the doping of the catalyst with copper, the methane conversion rose from 7.4 to 10.1%, and the benzene selectivities rose from 92.7 to 94.8%. The decrease in the catalyst activity slowed owing to the doping with copper.

B. M. Weckhuysen et al., (Journal of Catalysis 175, (1998) pages 338 to 346) studied the conversion of methane to benzene in the presence of transition metal-doped H-ZSM-5 zeolites. For this study, different pretreatments were carried out on commercially available H-ZSM-5 catalysts. The zeolites were subjected to a partial or full ion exchange by means of aqueous solutions which comprised ammonium nitrate and sodium chloride in different concentrations in order to obtain zeolites which are present in the H form completely, only partly or not at all. The zeolites were subsequently doped with Ga, Zn or Cr in conjunction with Ru or Pt, and also Mo, Cu, Zn and Fe. Methane conversions of from 0.2 to 7.9% coupled with benzene selectivities of 0 to nearly 80% were found.

The same group (B. M. Weckhuysen et al., Catalysis Letters 52 (1998), pages 31 to 36) produced a study of Mo/H-ZSM-5 catalysts with respect to the coke deposited on the catalyst in the DHAM of methane. The catalyst support used was commercially available H-ZSM-5 zeolite which had been converted fully to the H form by $NH_4$ exchange and calcination, and then impregnated with Mo and calcined again.

Coke deposits constitute a great problem for the industrial application of dehydroaromatizaton under nonoxidative conditions since they lower the activity of the catalyst within a relatively short time, which leads to short production cycles and a high regeneration demand. Frequently, coke deposits are additionally associated with a shortened lifetime of the catalyst. The regeneration of the catalyst is not unproblematic either, since the starting activities firstly have to be regularly re-establishable for an economically viable process and this secondly has to be possible over a large number of cycles.

Moreover, the coke deposits have an unfavorable effect on the mass balance and the yield, since each molecule of reactant which is converted to coke is no longer available for the desired reaction to give aromatics. The coke selectivities achieved to date in the prior art are in most cases more than 20% based on the aliphatic converted.

There is therefore a need for catalysts for the nonoxidative conversion of $C_1$-$C_4$-aliphatics, said catalysts having a lower coking tendency and a higher long-term stability than the catalysts known from the prior art. The catalysts should additionally be readily regenerable in order to enable long catalyst lifetimes.

The object is achieved by a molybdenum- and zeolite-comprising catalyst for dehydroaromatizing a reactant stream E comprising $C_1$-$C_4$-aliphatics, obtainable by the steps of I. treating a zeolite selected from the group of MFI and MWW with an $NH_4$-containing mixture with subsequent drying and calcination of the zeolite,
II. again treating the zeolite with an $NH_4$-containing mixture with subsequent drying of the zeolite,
III. applying the molybdenum and
IV. calcining.

The inventive catalysts are suitable in particular for nonoxidative dehydroaromatization of $C_1$-$C_4$-aliphatics, i.e. for preparing aromatic hydrocarbon compounds such as benzene and toluene from these alkanes under nonoxidative conditions. Significantly less coke is deposited on the inventive catalysts than on the catalysts known from the prior art. This firstly increases the service life of the catalysts before a regeneration of the catalyst becomes necessary; secondly, the reactant stream used can be utilized with greater economic viability, since less reactant is converted to coke which is harmful to the catalyst and lowers the yield. In the case of the inventive catalysts, the low selectivity for coke is associated with significantly higher conversions and/or higher benzene selectivities, which leads overall to higher benzene yields. A further great advantage of the inventive catalysts consists in their good regenerability. Even after several reaction and regeneration cycles, the initial activity of the catalyst in the first cycle is typically achieved again as a result of the regeneration.

According to the present invention, "nonoxidative conditions" means that the concentration of oxidizing agents such as oxygen or nitrogen oxides in the reactant stream E is below 5% by weight, preferably below 1% by weight, more preferably below 0.1% by weight. The mixture is most preferably free of oxygen. Likewise particularly preferred is a concentration of oxidizing agents in the mixture E which is equal to or lower than the concentration of oxidizing agents in the source from which the $C_1$-$C_4$-aliphatics originate.

The inventive catalysts comprise zeolites selected from the MFI and MWW structure types, more preferably ZSM-5 and MCM-22. Zeolites are aluminum silicates which are typically obtained in the sodium form when they are prepared. In the sodium form, the excess negative charge which is present in the crystal lattice owing to the exchange of tetravalent silicon atoms for trivalent aluminum atoms is balanced by sodium ions. Instead of sodium alone, the zeolite may also comprise further alkali metal and/or alkaline earth metal ions to balance the charge. The synthesis of the zeolites of the MFI and MWW structures is known to those skilled in the art. These zeolites can be prepared, for example, proceeding from alkali metal aluminate, alkali metal silicate and amorphous $SiO_2$ under hydrothermal conditions. In this synthesis, the type of channel systems formed in the zeolite can be controlled by means of organic template molecules, by means of the temperature and further experimental parameters.

Step I of the process, by which the inventive catalyst is obtainable, consists in converting the zeolite to the so-called H form. This means that the alkali metal and/or alkaline earth metal ions present in the zeolite are exchanged for protons. A customary process for converting catalysts to the H form, which is preferred according to the present invention, is a two-stage process in which the alkali metal and/or alkaline earth metal ions are first exchanged for ammonium ions. When the zeolite is heated to from about 400 to 500° C., the ammonium ion decomposes to volatile ammonia and to the proton which remains in the zeolite.

According to the present invention, in step I of the process, by which the inventive catalyst is obtainable, the zeolite is treated with an $NH_4$-containing mixture. The $NH_4$-containing component of the $NH_4$-containing mixture used is at least one ammonium salt selected from the group of ammonium halides, ammonium carbonate, ammonium hydrogencarbonate, ammonium nitrate, ammonium acetate, ammonium phosphate, ammonium hydrogenphosphate, ammonium dihydrogenphosphate, ammonium sulfate and ammonium hydrogensulfate. Preference is given to using ammonium nitrate as the $NH_4$-containing component.

The zeolite is treated with the $NH_4$-containing mixture by the known methods suitable for ammonium exchange of zeolites. These include, for example, impregnating, dipping or spraying the zeolite with an ammonium salt solution, the solution generally being used in excess. The solvents used are preferably water or alcohols. The mixture comprises typically from 1 to 20% by weight of the $NH_4$-component used. The treatment with the $NH_4$-containing mixture is carried out typically over a period of several hours and at elevated temperatures. After the action of the $NH_4$-containing mixture on the zeolite, excess mixture can be removed and the zeolite washed. Subsequently, the zeolite is dried at from 40 to 150° C. for several hours, typically from 4 to 20 hours. This is followed by the calcination of the zeolite at temperatures of from 300 to 700° C., preferably from 350 to 650° C. and more preferably from 500 to 600° C. The duration of the calcination is typically from 2 to 24 hours, preferably from 3 to 10 hours, more preferably from 4 to 6 hours.

In step II of the present process, by which the inventive catalyst is obtainable, the zeolite is again treated with an $NH_4$-containing mixture and then dried. The further treatment of the zeolite with the $NH_4$-containing mixture in step II of the process, by which the inventive catalyst is obtainable, is effected according to the above description for step I.

Commercially available zeolites in the H form have typically already passed through a first ammonium exchange by treatment with an $NH_4$-containing mixture and subsequent drying and calcination, i.e. step I of the process, by which the inventive catalyst is obtainable, has already been carried out by the manufacturer of the zeolite.

Therefore, it is possible in accordance with the invention to use commercially purchased zeolites of the MFI and MWW structure types, which are in the H form, directly in step II of the process according to the invention.

In one embodiment of the process, by which the inventive catalyst is obtainable, the zeolite which has been treated again with $NH_4$-containing mixture is additionally calcined between step II and step III. The calcination is effected under the conditions specified for the calcination in step I.

According to the invention, the further ammonium exchange serves not just to ensure very substantially complete exchange of the alkali metal and/or alkaline earth metal ions for protons, but additionally brings about structural changes in the zeolite. For example, the further treatment of the zeolite increases the Si:Al ratio, which is associated with a change in the ratio of Lewis-acidic sites to Brønsted-acidic sites. The increase in the Si:Al ratio is caused by a dealumination of the zeolite. Also illustrative of the changes in the zeolite by the further treatment is the increase in the BET surface area.

The catalysts of the present invention comprise molybdenum. According to the invention, this is applied to the zeolite by wet chemical or dry chemical means in step IV of the process.

In wet chemical methods, the molybdenum is applied in the form of aqueous, organic or organic-aqueous solutions of its salts or complexes by impregnating the zeolite with the appropriate solution. The solvent used may also be supercritical $CO_2$. The impregnation can be effected by the incipient wetness method, in which the porous volume of the zeolite is filled by about the same volume of impregnation solution and—if appropriate after maturation—the support is dried. It is also possible to work with an excess of solution, in which case the volume of this solution is greater than the porous volume of the zeolite. In this case, the zeolite is mixed with the impregnation solution and stirred for a sufficiently long period. In addition, it is possible to spray the zeolite with a solution of the molybdenum salt. Other preparation methods known to those skilled in the art are also possible, such as precipitation of the molybdenum onto the zeolite, spraying of a solution comprising a molybdenum compound, sol impregnation, etc. Particularly suitable molybdenum compounds are $(NH_4)_6Mo_7O_{24}$, $MoO_2$, $MoO_3$, $H_2MoO_4$, $Na_2MoO_4$, $(NH_3)_3Mo(CO)_3$ and $Mo(CO)_6$. After the molybdenum has been applied to the zeolite, the catalyst is dried under reduced pressure or under air at from about 80 to 130° C., typically for from 4 to 20 hours.

According to the invention, the molybdenum can also be applied by dry chemical methods, for example by depositing $Mo(CO)_6$, which is gaseous at relatively high temperatures, from the gas phase on the zeolite.

According to the invention, the catalyst comprises from 0.1 to 20% by weight, preferably from 0.2 to 15% by weight, more preferably from 0.5 to 10% by weight, based in each case on the total weight of the catalyst, of molybdenum.

In a preferred embodiment, the catalyst comprises at least one further element selected from the group of Mn, Cr, Nb, Ta, Zr, V, Zn, Ga, Cu, Ni, Fe and Co, more preferably selected from the group of Cu, Ni, Fe, Cr, Nb, Ta and Co, especially selected from the group of Cu, Ni, Fe, Nb, Ta and Co. Particular preference is given to catalysts which, as well as molybdenum, comprise Cu as a further element. In a further preferred embodiment, the catalyst comprises, as well as molybdenum, Ni as a further element. In a further preferred embodiment, the inventive catalyst comprises, as well as molybdenum, Fe as a further element.

According to the invention, the at least one further element in addition to molybdenum is present in the catalyst in a concentration of at least 0.1% by weight, based on the total weight of the catalyst. More preferably, the inventive catalysts comprise at least 0.2% by weight, most preferably at least 0.5% by weight, of at least one further element selected from Mn, Cr, Zr, Nb, Ta, V, Zn, Ga, Cu, Ni, Fe and Co, based on the total weight of the catalyst. The maximum amount of the further element or elements present in the inventive catalyst is, based in each case on the total weight of the catalyst, 10% by weight, preferably 5% by weight.

Preference is given in accordance with the invention to catalysts which comprise Cu as a further element. Preference is likewise given to catalysts which comprise Ni as a further element, and to catalysts which comprise Fe as a further element.

Especially preferred in accordance with the invention are catalysts which comprise from 0.1 to 20% by weight of molybdenum and at least 0.1% by weight of copper, based on the total weight of the catalyst. In a preferred embodiment of the present invention, the Mo- and Cu-containing catalysts comprise MCM-22 or ZSM-5 as the zeolite.

Also preferred in accordance with the invention are catalysts which comprise from 0.1 to 20% by weight of Mo and at least 0.1% by weight of Ni, more preferably from 0.1 to 20% by weight of Mo and from 0.5 to 2% by weight of Ni, based in each case on the total weight of the catalyst.

In a preferred embodiment of the present invention, the Mo- and Ni-containing catalysts comprise ZSM-5 as the zeolite.

In a preferred embodiment of the present invention, the Ni- and Cu-containing catalysts comprise ZSM-5 as the zeolite.

Equally preferred in accordance with the invention are catalysts comprising from 0.1 to 20% by weight and at least 0.1% by weight of Fe, more preferably from 0.1 to 20% by weight and from 0.5 to 20% by weight of Fe, based in each case on the total weight of the catalyst.

In a further embodiment the inventive catalyst comprises more than one further element selected from the group of Cu, Ni, Fe, Co, Mn, Cr, Nb, Ta, Zr, V, Zn and Ga, as well as Mo.

More preferably the catalyst comprises at least two further elements selected from the group of Cu, Ni, Fe, Co, Mn, Cr, Nb, Ta, Zr, V, Zn and Ga, as well as Mo.

Especially preferred catalysts comprise at least 0.1% by weight of a further element selected from the group of Mn, Cr, Nb, Ta, Zr, V, Zn, Ga, Cu, Ni, Fe and Co, preferably selected from the group of Fe, Co, Ni, Cu, Nb, Ta and Cr, and at least 0.05% by weight of a second further element selected from the group of Cu, Ni, Fe, Co, Cr, Nb, Ta, Zr, V, Zn and Ga, preferably selected from the group of Fe, Co, Ni, Cu, Nb, Ta and Cr, as well as molybdenum, based in each case on the total weight of the catalyst.

Preferred in accordance with the invention are the combinations of Mo, Cu, Nb; Mo, Ni, Nb; Mo, Ni, Ta; Mo, Ni, Fe; Mo, Ni, Cr and Mo, Cu, Fe.

The elements Mn, Cr, Zr, V, Zn, Ga, Cu, Ni, Fe, Nb, Ta and Co are typically applied to the zeolite by wet chemical means. These elements are applied to the zeolite analogously to the procedure described for the wet chemical application of molybdenum. The metal salts used are preferably the nitrates such as copper nitrate, nickel nitrate, iron nitrate and cobalt nitrate, but it is also possible to use other salts known to those skilled in the art for wet chemical application. These include the ammonium metalates, halides, especially chloride, acetate, alkaline carbonates, formate, tartrate, complexes with ligands such as acetylacetonate, amines, aminoalcohols, diols, polyols, EDTA, carboxylates such as oxalate and citrate, and hydroxycarboxylic acid salts. It is equally possible to apply the elements to the support as a fine carbide powder, the general assumption being that molybdenum carbide constitutes the reactive species in the catalyst in the dehydroaromatization.

When the molybdenum is applied by wet chemical means in step III, the at least one further element can be applied together with the molybdenum. However, it is also possible to apply the further element and the molybdenum in succession, in which case each application is followed by drying. It may also be advantageous to observe a certain sequence in the course of application. When the catalyst comprises more than one further element, the molybdenum and the further elements can likewise be applied together or else successively, in which case the zeolite is dried between each of the different applications. Here too, it may be advantageous to apply the individual elements and the molybdenum in a certain sequence.

When the molybdenum is applied by a dry chemical route in step III, the impregnation with the at least one further element is typically effected before step III. If more than one further element is applied, these elements can be applied together or else successively, in which case drying is effected between the individual impregnation stages. It may be advantageous to apply the individual elements in a certain sequence.

In a preferred embodiment of the invention, the solution with which the molybdenum and if appropriate the further elements are applied to the zeolite comprises at least one complexing agent. The complexing agent is preferably selected from the group of ammonia, acetyl acetonate, amines, aminoalcohols, EDTA, carboxylates such as oxalate and citrate, and hydroxycarboxylic acid salts. Particular preference is given to using EDTA. The presence of the complexing agent in the impregnating solution has an advantageous effect on the catalyst activity.

When the inventive catalyst, in one of the above-described embodiments, comprises at least two further elements selected from the group Fe, Co, Ni, Cu, Cr, Nb, Ta, Mn, Zr, V, Zn and Ga, a preferred embodiment of the invention comprises applying the Mo to the zeolite together with at least one of the further elements in the presence of a complexing agent as an impregnating solution, then drying the zeolite, and applying the second or the further elements with the aid of an impregnating solution.

When the inventive catalyst as described above comprises at least one further element as well as molybdenum, the catalyst is obtainable by the steps of
I. treating a zeolite selected from the group of MFI and MWW with an $NH_4$-containing mixture, with subsequent drying and calcination of the zeolite,
II. again treating the zeolite with an $NH_4$-containing mixture, with subsequent drying and calcination of the zeolite,
III. applying the molybdenum and at least one further element selected from the group of Mn, Cr, Nb, Ta, Zr, V, Zn, Ga, Cu, Ni, Fe and Co and
IV. calcining.

After the Mo and if appropriate the further elements have been applied, in step IV of the process, by which the inventive catalyst is preparable, the catalyst is calcined. The calcination is carried out under the conditions described above for the calcination which proceeds in step I.

In a further preferred embodiment of the present invention, the catalyst is mixed with an Si-containing binder between step I and II or between step II and III. Suitable Si-containing binders are especially tetraalkoxysilanes, polysiloxanes and colloidal $SiO_2$ sols.

When the Si-containing binders are mixed with the zeolite before step II, i.e. before the further treatment of the zeolite with an $NH_4$-containing mixture, step II is preceded by a calcination under the customary conditions. According to the invention, addition of the Si-containing binder is followed by a shaping step in which the catalyst material is processed by processes known to those skilled in the art to give shaped bodies. Shaping processes include, for example, spraying of a suspension comprising the zeolite or the catalyst material, tableting, pressing in the moist or dry state, and extrusion. Two or more of these processes can also be combined. For the shaping, it is possible to use assistants such as pore formers and pasting agents, or else other additives known to those skilled in the art. Possible pasting agents are those compounds which lead to improvement in the mixing, kneading and flow properties. In the context of the present invention, these are preferably organic, especially hydrophilic, polymers, for example cellulose, cellulose derivatives such as methylcellulose, starch such as potato starch, wallpaper paste, acrylates, polyacrylates, polymethacrylates, polyvinyl alcohols, polyvinylpyrrolidone, polyisobutylene, polytetrahydrofuran, polyglycol ether, fatty acid compounds, wax emulsions, water or mixtures of two or more of these compounds. In the context of the present invention, pore formers include, for example, compounds which are dispersible, suspendable or emulsifiable in water or aqueous solvent mixtures, such as polyalkylene oxides, polystyrene, polyacrylates, polymethacrylates, polyolefins, polyamides, polyesters, carbohydrates, cellulose, cellulose derivatives, for example methylcellulose, natural sugar fibers, pulp, graphite or mixtures of two or more of these compounds. Pore formers and/or pasting agents are preferably removed from the resulting shaped body by at least one suitable drying and/or calcination step after the shaping.

The geometry of the catalysts obtainable in accordance with the invention may, for example, be spherical (hollow or solid), cylindrical (hollow or solid), annular, saddle-shaped, star-shaped, honeycomb-shaped or tablet-shaped. In addition, extrudates are useful, for example in strand form, trilobal form, quatrolobal form, star form or hollow cylindrical form. In addition, the catalyst material to be shaped can be extruded and calcined, and the extrudates thus obtained can be crushed and processed to spall or powder. The spall can be separated into different screen fractions. A preferred screen fraction has the particle size from 0.25 to 0.5 mm.

In a preferred embodiment of the invention, the catalyst is used in the form of shaped bodies or spall.

In a further preferred embodiment, the catalyst is used in the form of powder. The catalyst powder may comprise Si-containing binder, but may also be present free of Si-containing binder.

When the inventive catalyst comprises an Si-containing binder, it is present in a concentration of from 5 to 60% by weight, based on the total weight of the catalyst, preferably from 10 to 40% by weight, more preferably from 15 to 30% by weight.

The present invention further provides a process for preparing a molybdenum- and zeolite-comprising catalyst as described above, comprising the steps of
I. treating a zeolite selected from the group of MFI and MWW with an $NH_4$-containing mixture with subsequent drying and calcination of the zeolite,
II. again treating the zeolite with an $NH_4$-containing mixture with subsequent drying of the zeolite,
III. applying the molybdenum and
IV. calcining.

When the inventive catalyst as described above comprises at least one further element as well as molybdenum, the process according to the invention for preparing the catalyst comprises the steps of
I. treating a zeolite selected from the group of MFI and MWW with an $NH_4$-containing mixture, with subsequent drying and calcination of the zeolite,
II. again treating the zeolite with an $NH_4$-containing mixture, with subsequent drying of the zeolite,
III. applying the molybdenum and at least one further element selected from the group of Mn, Cr, Nb, Ta, Zr, V, Zn, Ga, Cu, Ni, Fe and Co and
IV. calcining.

The present invention likewise provides for the use of the above-described inventive catalyst for dehydroaromatizing a reactant stream E comprising $C_1$-$C_4$-aliphatics.

It may be advantageous to activate the catalyst used for dehydroaromatization of $C_1$-$C_4$-aliphatics before the actual reaction.

This activation can be effected with a $C_1$-$C_4$-alkane, for example methane, ethane, propane, butane or a mixture thereof, preferably butane. The activation is carried out at a temperature of from 250 to 650° C., preferably at from 350 to 550° C., and a pressure of from 0.5 to 5 bar, preferably from 0.5 to 2 bar. Typically, the GHSV (gas hourly space velocity) in the activation is from 100 to 4000 h$^{-1}$, preferably from 500 to 2000 h$^{-1}$.

However, it is also possible to carry out an activation by virtue of the reactant stream E already comprising the $C_1$-$C_4$-alkane, or a mixture thereof, per se, or by adding the $C_1$-$C_4$-alkane, or a mixture thereof, to the reactant stream E. The activation is carried out at a temperature of from 250 to 650° C., preferably at from 350 to 550° C., and a pressure of from 0.5 to 5 bar, preferably from 0.5 to 2 bar. Typically, the GHSV (gas hourly space velocity) in the activation is from 100 to 4000 h$^{-1}$, preferably from 500 to 2000 h$^{-1}$.

In a further embodiment, it is also additionally possible to add hydrogen to the $C_1$-$C_4$-alkane. The activation can also be carried out only with methane as the $C_1$-$C_4$-alkane.

In a preferred embodiment of the present invention, the catalyst is activated with an $H_2$-comprising gas stream which may additionally comprise inert gases such as $N_2$, He, Ne and/or Ar.

The present invention further provides a process for dehydroaromatizing a reactant stream E comprising $C_1$-$C_4$-aliphatics by reacting the reactant stream E in the presence of a molybdenum- and zeolite-comprising catalyst as described above, which is obtainable by the steps of I. treating a zeolite selected from the group of MFI and MWW with an $NH_4$-containing mixture with subsequent drying and calcination of the zeolite,
II. again treating the zeolite with an $NH_4$-containing mixture with subsequent drying of the zeolite,
III. applying the molybdenum and
IV. calcining.

The present invention likewise provides the process for dehydroaromatizing a reactant stream E comprising $C_1$-$C_4$-aliphatics by reacting the reactant stream E in the presence of a molybdenum- and zeolite-comprising catalyst as described above, which is obtainable by the steps of I. treating a zeolite selected from the group of MFI and MWW with an $NH_4$-containing mixture, with subsequent drying and calcination of the zeolite,
II. again treating the zeolite with an $NH_4$-containing mixture, with subsequent drying of the zeolite,
III. applying the molybdenum and at least one further element selected from the group of Mn, Cr, Nb, Ta, Zr, V, Zn, Ga, Cu, Ni, Fe and Co and
IV. calcining.

According to the invention, the reactant stream E comprises at least one aliphatic having from 1 to 4 carbon atoms. These aliphatics include methane, ethane, propane, n-butane, i-butane, propene, 1- and 2-butene and isobutene. In one embodiment of the invention, the reactant stream E comprises at least 50 mol %, preferably at least 60 mol %, more preferably at least 70 mol %, exceptionally preferably at least 80 mol %, especially at least 90 mol %, of $C_1$-$C_4$-aliphatics.

Among the aliphatics, particular preference is given to using the saturated alkanes; in that case, reactant stream E comprises preferably at least 50 mol %, preferably at least 60 mol %, more preferably at least 70 mol %, exceptionally preferably at least 80 mol %, especially at least 90 mol %, of alkanes having from 1 to 4 carbon atoms.

Among the alkanes, methane and ethane are preferred, especially methane. In this embodiment of the present invention, the reactant stream E comprises preferably at least 50 mol %, preferably at least 60 mol %, more preferably at least 70 mol %, exceptionally preferably at least 80 mol %, especially at least 90 mol %, of methane.

The source used for the $C_1$-$C_4$-aliphatics is preferably natural gas. The typical composition of natural gas is as follows: 75 to 99 mol % of methane, 0.01 to 15 mol % of ethane, 0.01 to 10 mol % of propane, up to 6 mol % of butane and higher hydrocarbons, up to 30 mol % of carbon dioxide, up to 30 mol % of hydrogen sulfide, up to 15 mol % of nitrogen and up to 5 mol % of helium. Before use in the process according to the invention, the natural gas can be purified and enriched by methods known to those skilled in the art. The purification includes, for example, the removal of any hydrogen sulfide or carbon dioxide present in the natural gas and of further compounds which are undesired in the subsequent process.

The $C_1$-$C_4$-aliphatics present in the reactant stream E may also stem from other sources, for example may have originated in the course of crude oil refining. The $C_1$-$C_4$-aliphatics may also have been produced by renewable means (e.g. biogas) or synthetic means (e.g. Fischer-Tropsch synthesis).

If the $C_1$-$C_4$-aliphatic source used is biogas, the reactant stream E may additionally also comprise ammonia, traces of lower alcohols and further additives typical of biogas.

In a further embodiment of the process according to the invention, the reactant stream E used may be LPG (liquid petroleum gas). In a further embodiment of the process according to the invention, the reactant stream E used may be LNG (liquefied natural gas).

It is additionally possible to add hydrogen, steam, carbon monoxide, carbon dioxide, nitrogen and one or more noble gases to the reactant stream E.

According to the invention, the dehydroaromatization of $C_1$-$C_4$-aliphatics is carried out in the presence of the above-described, inventive catalysts at temperatures of from 400 to 1000° C., preferably from 500 to 900° C., more preferably from 600 to 800° C., especially from 650 to 750° C., at a pressure of from 0.5 to 100 bar, preferably at from 1 to 50 bar, more preferably at from 1 to 30 bar, especially from 1 to 10 bar. According to the present invention, the reaction is carried out at a GHSV (gas hourly space velocity) of from 100 to 10 000 h$^{-1}$, preferably from 200 to 3000 h$^{-1}$.

It will be appreciated that the catalysts used in the dehydroaromatization in accordance with the invention, in the event of declining activity, can be regenerated by customary methods known to those skilled in the art. Especially preferred according to the present invention is the regeneration of the catalysts with hydrogen. This can be done, for example, by adding hydrogen to the reactant stream E. The ratio of reactant stream E to hydrogen stream is typically in the range from 1:1000 to 1:1, preferably from 1:500 to 1:5; the ratio is, however, preferably selected such that a gas stream comprising at least 95 mol % of hydrogen is used for regeneration. However, it may also be possible to pass reactant stream E and hydrogen over the catalyst in alternation.

Especially the inventive catalysts which comprise at least one further element selected from the group of Cu, Ni, Fe and Co can be regenerated efficiently by means of hydrogen.

The dehydroaromatization of $C_1$-$C_4$-aliphatics can in principle be carried out in all reactor types known from the prior art. A suitable reactor form is the fixed bed reactor, tubular reactor or tube bundle reactor. In these reactors, the catalyst is present as a fixed bed in one reaction tube or in a bundle of reaction tubes. The inventive catalysts may likewise be used in the form of a fluidized bed or moving bed in the corresponding reactor types suitable for this purpose, and the process according to the invention for dehydroaromatization can be carried out with the catalysts in such a form.

The present invention will be illustrated in detail hereinafter with reference to examples.

A Treatment of a Zeolite with an $NH_4$-Containing Mixture 100 g of a commercially available ZSM-5 zeolite in H form are mixed with 100 g of ammonium nitrate and 900 g of water, and heated at 80° C. in a stirred apparatus for 2 hours. After cooling, the suspension is filtered and washed with water. The filter cake is dried at 120° C. overnight.

B Mixing of the Zeolite with an Si-Containing Binder and Shaping 100 g of a ZSM-5 zeolite are mixed with 10 g of sodium carboxymethylcellulose and, after adding 30 g of an Si-containing binder (Silres® MSE 100 from Wacker Silicones), kneaded with addition of approx. 100 ml of water in portions for 60 minutes. The material thus obtained is extruded through a die with round cross section (diameter 2 mm) and the resulting extrudates are dried at 120° C. and calcined at 500° C. for 5 hours. The extrudates thus obtained are crushed and a screen fraction of from 0.25 to 0.5 mm is removed and is then correspondingly used further.

EXAMPLES 1 AND 2

Using two different H-ZSM-5 zeolites, the influence of the $NH_4$ treatment and the shaping is studied. Table 1 shows the Si:Al ratios of the zeolite with the designation H-ZSM-5 PZ2-50 in the H form without treatment, with $NH_4$ treatment, with $NH_4$ treatment and formation of spall, and of a sample which has first been processed to spall and then treated with $NH_4$; Table 2 shows the results for the zeolite H-ZSM-5 PZ2-25. The Si:Al ratio was determined by means of elemental analysis.

TABLE 1

| | Si:Al [mol:mol] |
|---|---|
| H-ZSM-5 PZ2-50, untreated, powder | 19.5 |
| H-ZSM-5 PZ2-50-H with $NH_4$ treatment, powder | 24.7 |
| H-ZSM-5 PZ2-50-H with $NH_4$ treatment, then shaped to spall | 25.6 |
| H-ZSM-5 PZ2-50-H with $NH_4$ treatment of spall | 26.3 |

TABLE 2

| | Si:Al [mol:mol] |
|---|---|
| H-ZSM-5 PZ2-25, untreated, powder | 13.8 |
| H-ZSM-5 PZ2-25 with $NH_4$ treatment, powder | 14.2 |
| H-ZSM-5 PZ2-25 with $NH_4$ treatment, then shaped to spall | 17.0 |

EXAMPLE 3

Characterization of the Microstructure

The microstructure of the untreated and $NH_4NO_3$-treated H-ZSM-5 PZ2-25 zeolites was determined by means of nitrogen sorption (Quantachrom Autosorb). The nitrogen was adsorbed at −196° C.; the outgassing temperature was 200° C.; the outgassing time was 14 hours. The (total) pore volume indicates the pore volume of all pores having a diameter below 335.47 nm. Micropores are considered to be pores having a diameter of from 0 to 2 nm, mesopores to be pores having a diameter of from 2 to 50 nm, and macroporous pores to be those having a pore diameter of >50 nm (IUPAC).

Table 3 shows the results of the characterization of the microstructure of the zeolites.

TABLE 3

| Sample designation | Form | BET surface area (m²/g) | Total pore volume (cm³/g) | Micropore volume (cm³/g) | Meso- and macropore volume (cm³/g) |
|---|---|---|---|---|---|
| H-ZSM-5 HPZ2-25 | Powder | 303 | 0.556 | 0.141 | 0.415 |
| H-ZSM-5 HPZ2-25 | $NH_4$ treatment (A) powder | 337 | 0.647 | 0.156 | 0.491 |
| H-ZSM-5 HPZ2-25 | $NH_4$ treatment (A) spall (B) | 336 | 0.424 | 0.151 | 0.273 |

The treatment with $NH_4NO_3$ increases the BET surface area and the Si:Al ratio significantly. The micropore volume is found to be relatively unchanged as a result of the pretreatment; spall generation reduces the proportion of meso- and macropores significantly.

C to I describe the impregnation of the zeolite with molybdenum and if appropriate further elements, and the test method for the catalyst.

C Impregnation of the Zeolite, Which May Have Been Pretreated According to A and/or B, with Aqueous Ammonium Hepta Molybdate Solution 100 g of the zeolite support which may have been pretreated with $NH_4$ according to A and/or B are initially charged in a dish. Approx. 12 g of ammonium heptamolybdate tetrahydrate (>98%, from ABCR) are made up with water to the corresponding volume of water absorption (approx. 100 ml) of the zeolite and stirred until complete dissolution. The solution is subsequently added to the zeolite with stirring and the material is mixed further at room temperature for 15 min. The material is subsequently heated to 120° C. in a drying cabinet, dried overnight and then calcined at 500° C. for 4 or 5 h.

D Stepwise Impregnation of the Zeolite, which May Have Been Pretreated According to A and/or B, with Mo Solution, Drying, and Impregnation with an Aqueous Solution Comprising Ni Salt, Cu Salt, Cr Salt or Fe Salt 100 g of a zeolite (which may have been pretreated with $NH_4NO_3$ according to A and/or B) are impregnated with molybdenum according to C, but finally only dried and not calcined. The corresponding, Mo-laden zeolite is initially charged in a dish. For impregnation with Cu, 4.1 g of copper (II) nitrate 2.5-hydrate (>99%, from Riedel-de Haën) are made up with water to the corresponding volume of water absorption (approx. 100 ml) of the zeolite and stirred until complete dissolution. The solution is subsequently added to the zeolite with stirring and the material is mixed further at room temperature for 15 min. The material is then heated to 120° C. in a drying cabinet, dried overnight and then calcined at 500° C. for 4 or 5 h. If impregnation is to be effected with Ni instead of Cu, 5.4 g of nickel(II) nitrate hexahydrate (>99%, from Riedel-de Haën) is used as the Ni salt instead of the copper(II) nitrate 2.5-hydrate. Iron(III) nitrate nonahydrate (>99%, from Riedel-de Haën) is used for impregnation with Fe, and chromium(III) nitrate nonahydrate (>99%, from Riedel-de Haën) for impregnation with Cr.

E Stepwise Impregnation of the Zeolite, Which May Have Been Pretreated According to A and/or B, with an Aqueous Solution Comprising Ni Salt, Cu Salt, Cr Salt or Fe Salt, Drying and Impregnation with Mo Solution 100 g of a zeolite (which may have been pretreated with $NH_4NO_3$ according to A and/or B) are initially charged in a dish. Approx. 4.1 g of copper(II) nitrate 2.5-hydrate (>99%, from Riedel-de Haën) are made up with water to the corresponding volume of water absorption (approx. 100 ml) of the zeolite and stirred until complete dissolution. If impregnation is to be effected with Ni instead of Cu, 5.4 g of nickel(II) nitrate hexahydrate (>99%, from Riedel-de Haën) is used as the Ni salt instead of the copper(II) nitrate 2.5-hydrate. Iron (III) nitrate nonahydrate (>99%, from Riedel-de Haën) is used for impregnation with Fe, and chromium(III) nitrate nonahydrate (>99%, from Riedel-de Haën) for impregnation with Cr. The solution is subsequently added to the zeolite with stirring and the material is mixed further at room temperature for 15 min. The material is subsequently heated to 120° C. in a drying cabinet and dried overnight, but not calcined. Subsequently, the already Cu-laden catalyst is impregnated with Mo according to C.

F Impregnation of the Zeolite, which May Have Been Pretreated According to A and/or B, with a Solution Comprising Ammonium Heptamolybdate and a Salt of a Further Element (Ni, Cu, Cr, Fe)

100 g of the zeolite (which may have been pretreated with $NH_4NO_3$ according to A and/or B) are initially charged in a dish. Approx. 12 g of ammonium heptamolybdate tetrahydrate (>98%, from ABCR) and 4.1 g of copper(II) nitrate 2,5-hydrate (>99%, from Riedel-de Haën) are made up with water to the corresponding volume of water absorption (approx. 100 ml) of the zeolite and stirred until complete dissolution. If impregnation is to be effected with Ni instead of Cu, 5.4 g of nickel(II) nitrate hexahydrate (>99%, from Riedel-de Haën) is used as the Ni salt instead of the copper(II) nitrate 2.5-hydrate. Iron(III) nitrate nonahydrate (>99%, from Riedel-de Haën) is used for impregnation with Fe, and chromium(III) nitrate nonahydrate (>99%, from Riedel-de Haën) for impregnation with Cr. The solution is subsequently added to the zeolite with stirring and the material is mixed further at room temperature for 15 min. The material is subsequently heated to 120° C. in a drying cabinet, dried overnight and then calcined at 500° C. for 4 or 5 h.

G Catalytic Test Under Standard Conditions

Approx. 1.6 g of the catalyst are heated to 500° C. under a helium atmosphere in a reactor tube (internal diameter=4 mm). At this temperature, methane is switched on and the catalyst is kept at this temperature for 30 min before it is brought to the reaction temperature of 700° C. under methane comprising 10% by volume of helium. The catalyst is then operated at 700° C., 1 bar, 10% by volume of He in methane and a GHSV of 500 $h^{-1}$ for approx. 10 h.

This period can optionally be followed by regeneration with $H_2$. To this end, brief inertization with helium is followed by conduction of pure hydrogen through the reactor at a reaction temperature of from 700° C. to 740° C. and a pressure of from 1 to 5 bar for 2 to 3 h, then again by inertization with $H_2$, and the reaction mixture is introduced at 700° C., 1 bar, 10% by volume of He in methane.

H Impregnation of the Zeolite, Which May Have Been Pretreated According to A and/or B, According to F, a Complexing Agent Having Been Added to the Hot Aqueous Impregnating Solution I Impregnation of the Zeolite, Which May Have Been Pretreated According to A and/or B, Drying of the Zeolite, and Further Impregnation with an Aqueous Solution Comprising an Fe Salt, Cr Salt or Nb Salt or Ta Carbide

EXAMPLE 4

6% by Weight of Mo on H-ZSM-5 (Powder) (Noninventive)

The catalyst was prepared according to C on a commercial H-ZSM-5 (ZEOcat PZ-2/50-H, from ZEOCHEM, $SiO_2$:$Al_2O_3$=approx. 50 mol/mol) and tested according to G.

EXAMPLE 5

6% by Weight of Mo on H-ZSM-5 (Powder) (Inventive)

A commercial H-ZSM-5 (ZEOcat PZ-2/50-H, from ZEOCHEM, $SiO_2$:$Al_2O_3$=approx. 50 mol/mol) support was pretreated according to A. The catalyst was prepared from the support thus obtained according to C and tested according to G.

EXAMPLE 6

6% by Weight of Mo/1% by Weight of Cu on H-ZSM-5 (Powder) (Noninventive)

The catalyst was prepared according to F on a commercial H-ZSM-5 (ZEOcat PZ-2/50-H, from ZEOCHEM, $SiO_2$:$Al_2O_3$=approx. 50 mol/mol) and tested according to G.

EXAMPLE 7

6% by Weight of Mo on H-ZSM-5 (Spall) (Noninventive)

A commercial H-ZSM-5 (ZEOcat PZ-2/50-H, from ZEOCHEM, $SiO_2$:$Al_2O_3$=approx. 50 mol/mol) support was shaped to spall according to B. The catalyst was prepared from the spall thus obtained according to C and tested according to G.

EXAMPLE 8

6% by Weight of Mo/1% by Weight of Cu on H-ZSM-5 (Spall) (Noninventive)

A commercial H-ZSM-5 (ZEOcat PZ-2/50-H, from ZEOCHEM, $SiO_2$:$Al_2O_3$=approx. 50 mol/mol) support was shaped to spall according to B. The catalyst was prepared from the support thus obtained according to F and tested according to G.

EXAMPLE 9

6% by Weight of Mo on H-ZSM-5 (Spall) (Inventive)

A commercial H-ZSM-5 (ZEOcat PZ-2/50-H, from ZEOCHEM, $SiO_2$:$Al_2O_3$=approx. 50 mol/mol) support was pretreated according to A and then shaped to spall according to B. The catalyst was prepared from the spall thus obtained according to C and tested according to G.

EXAMPLE 10

6% by Weight of Mo/1% by Weight of Cu on H-ZSM-5 (Spall) (Inventive)

A commercial H-ZSM-5 (ZEOcat PZ-2/50-H, from ZEOCHEM, $SiO_2$:$Al_2O_3$=approx. 50 mol/mol) support was pretreated according to A and then shaped to spall according to B. The catalyst was prepared from the spall thus obtained according to D and tested according to G.

EXAMPLE 11

6% by weight of Mo/1% by Weight of Cu on H-ZSM-5 (Spall) (Inventive)

A commercial H-ZSM-5 (ZEOcat PZ-2/50-H, from ZEOCHEM, $SiO_2:Al_2O_3$=approx. 50 mol/mol) support was pretreated according to A and then shaped to spall according to B. The catalyst was prepared from the spall thus obtained according to F and tested according to G.

EXAMPLE 12

6% by Weight of Mo/1% by Weight of Cu on H-ZSM-5 (Spall) (Inventive)

A commercial H-ZSM-5 (ZEOcat PZ-2/50-H, from ZEOCHEM, $SiO_2:Al_2O_3$=approx. 50 mol/mol) support was pretreated according to A and then shaped to spall according to B. The catalyst was prepared from the spall thus obtained according to E and tested according to G.

EXAMPLE 13

6% by Weight of Mo/1% by Weight of Ni on H-ZSM-5 (Spall) (Inventive)

A commercial H-ZSM-5 (ZEOcat PZ-2/50-H, from ZEOCHEM, $SiO_2:Al_2O_3$=approx. 50 mol/mol) support was pretreated according to A and B. The catalyst was prepared from the spall thus obtained according to F, using 20 g of zeolite, approx. 2.4 g of the molybdate compound and approx. 1.06 g of nickel(II) nitrate hexahydrate (>99%, from Riedel-de Haën) with approx. 20 ml of water. The catalyst was tested according to G.

EXAMPLE 14

6% by Weight of Mo/1% by Weight of Cu on H-MCM-22 (Spall) (Inventive)

An H-MCM-22 zeolite (Si:Al=approx. 50 mol/mol) support was pretreated according to A and then shaped to spall according to B. The catalyst was prepared from the spall thus obtained according to F and tested according to G.

TABLE 4

Comparison of the catalytic performance of the catalysts from Examples 1 to 13 (zeolite: H-ZSM-5 where $SiO_2:Al_2O_3$ = approx. 50)

| Catalyst example | Catalytically active metals | Preparation | Conversion after 7 h [%] | Benzene selectivity after 7 h [%] | Coke selectivity after 7 h [%] |
|---|---|---|---|---|---|
| 4 | 6% by weight Mo | C | 2.0 | 1 | 72 |
| 5 | 6% by weight Mo | A, C | 9.8 | 62 | 27 |
| 6 | 6% by weight Mo, 1% by weight Cu | F | 8.7 | 64 | 21 |
| 7 | 6% by weight Mo | B, C | 4.7 | 19 | 54 |
| 8 | 6% by weight Mo, 1% by weight Cu | B, F | 5.8 | 58 | 23 |
| 9 | 6% by weight Mo | A, B, C | 11 | 61 | 12 |
| 10 | 6% by weight Mo, 1% by weight Cu | A, B, D | 10.5 | 57 | 12 |
| 11 | 6% by weight Mo, 1% by weight Cu | A, B, F | 7.6 | 64 | 8 |
| 12 | 6% by weight Mo, 1% by weight Cu | A, B, E | 7.4 | 64 | 19 |
| 13 | 6% by weight Mo, 1% by weight Ni | A, B, F | 10.8 | 68 | 4 |

Conversion: proportion of methane converted based on methane used in percent
Benzene selectivity: proportion of benzene based on methane converted in percent
Coke selectivity: proportion of coke deposits based on methane converted in percent The inventive catalysts, each of which comprise a zeolite which has been treated twice with an $NH_4$-containing solution (treatment according to A, Examples 5 and 9 to 13), exhibit high benzene selectivities coupled with low coke selectivities and high methane conversions.

TABLE 5

Comparison of the catalytic performance of the catalysts from Examples 11 (zeolite: H-ZSM-5) and 14 (zeolite: H-MCM-22)

| Catalyst example | Catalytically active metals | Preparation | Conversion after 5 h [%] | Benzene selectivity after 5 h [%] | Coke selectivity after 5 h [%] |
|---|---|---|---|---|---|
| 14 | 6% by weight Mo, 1% by weight Cu | A, B, F | 9.7 | 71 | 3 |
| 11 | 6% by weight Mo, 1% by weight Cu | A, B, F | 11.2 | 57 | 4 |

The two inventive catalysts differ in the zeolite used; in Example 11, a ZSM-5 zeolite was used, in Example 14 an MCM-22 zeolite. The two catalysts exhibit, in comparison to the noninventive catalysts shown in Table 4, extremely low coke selectivities, though it should be taken into account when comparing with the values in Table 4 that the data shown there were recorded after 7 h of reaction time, those from Table 5 after 5 h of reaction time. The catalyst comprising Mo and Cu on MCM-22 has a significantly higher selectivity for benzene and a slightly reduced selectivity for coke compared with the ZSM-5-containing catalyst.

EXAMPLE 15

6% by Weight of Mo/1% by Weight of Cu on H-ZSM-5 (Spall) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to F, using 10 g of zeolite, approx. 1.2 g of the molybdate compound and 0.41 g of copper(II) nitrate 2,5-hydrate (>99%, from Riedel-de Haën) with approx. 100 ml of water. The catalyst was tested according to G.

EXAMPLE 16

6% by Weight of Mo/1% by Weight of Cu on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to H, using 15 g of zeolite, approx. 1.8 g of the molybdate compound and 0.6 g of copper(II) nitrate 2,5-hydrate (>99%, from Riedel-de Haën) and approx. 1.6 g of ethylenediaminetetraacetic acid (EDTA, >99.9%, from Aldrich) with approx. 19 ml of water. The catalyst was tested according to G.

EXAMPLE 17

6% by Weight of Mo/1% by Weight of Ni on H-ZSM-5 (Spall) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to F, using 20 g of zeolite, approx. 2.4 g of the molybdate compound and 1.1 g of nickel(II) nitrate hexahydrate (>99%, from Riedel-de Haën) with approx. 20 ml of water. The catalyst was tested according to G.

EXAMPLE 18

6% by Weight of Mo/1% by Weight of Ni on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to H, using 20 g of zeolite, approx. 2.4 g of the molybdate compound and 1.1 g of nickel(II) nitrate hexahydrate (>99%, from Riedel-de Haën) and approx. 1.6 g of ethylenediaminetetraacetic acid (EDTA, >99.9%, from Aldrich) with approx. 20 ml of water. The catalyst was tested according to G.

TABLE 6

Comparison of the catalytic performance of the catalysts from Examples 15 to 18 (influence of the complexing agent, zeolite: H-ZSM-5 with $SiO_2:Al_2O_3$ = approx. 25:1)

| Catalyst example | Catalytically active metals | Preparation | Complexing agent | Conversion after 7 h [%] | Benzene selectivity after 7 h [%] | Coke selectivity after 7 h [%] |
|---|---|---|---|---|---|---|
| 15 | 6% by weight Mo, 1% by weight Cu | A, B, F | none | 10.1 | 55 | 23 |
| 16 | 6% by weight Mo, 1% by weight Cu | A, B, H | EDTA | 9.6 | 64 | 27 |
| 17 | 6% by weight Mo, 1% by weight Ni | A, B, F | none | 10.6 | 51 | 27 |
| 18 | 6% by weight Mo, 1% by weight Ni | A, B, H | EDTA | 9.1 | 68 | 21 |

The addition of the EDTA complexing agent in the impregnation of the catalysts with the metals Mo and Cu or Ni brings about a significant increase in the benzene selectivities.

EXAMPLE 19

6% by Weight of Mo on H-ZSM-5 (Spall) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to C, using 15 g of zeolite and approx. 1.8 g of the molybdate compound with approx. 15 ml of water. The catalyst was tested according to G.

EXAMPLE 20

6% by weight of Mo/1% by Weight of Fe on H-ZSM-5 (Spall) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to D, using 15 g of zeolite and approx. 1.8 g of the molybdate compound with approx. 17 ml of water. The catalyst was tested according to G. The material was heated to 120° C. in a drying cabinet and dried overnight. Then approx. 1.2 g of iron(III) nitrate nonahydrate (>99%, from Riedel-de Haën) were dissolved in a further approx. 17 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 21

6% by Weight of Mo/1% by Weight of Cu on H-ZSM-5 (Spall) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to F, using 100 g of zeolite, approx. 12 g of the molybdate compound and 4.1 g of copper(II) nitrate 2.5-hydrate (>99%, from Riedel-de Haën) with approx. 100 ml of water. The catalyst was tested according to G.

EXAMPLE 22

6% by Weight of Mo/1% by Weight of Cu on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to H, using 15 g of zeolite, approx. 1.8 g of the molybdate compound and 0.6 g of copper(II) nitrate 2.5-hydrate (>99%, from Riedel-de Haën) and approx. 1.2 g of ethylenediaminetetraacetic acid (EDTA, >99.9%, from Aldrich) with approx. 17 ml of hot water. The catalyst was tested according to G.

EXAMPLE 23

6% by Weight of Mo/1% by Weight of Cu on H-ZSM-5 (Spall, $NH_3$) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to H, using 15 g of zeolite, approx. 1.8 g of the molybdate compound, 0.6 g of copper(II) nitrate 2.5-hydrate (>99%, from Riedel-de Haën) with approx. 17 ml of 25% aqueous ammonia solution. The catalyst was tested according to G.

EXAMPLE 24

6% by Weight of Mo/1% by Weight of Cu/1% by Weight of Fe on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to I, using 15 g of zeolite, approx. 1.8 g of the molybdate compound, 0.6 g of copper(II) nitrate 2.5-hydrate (>99%, from Riedel-de Haën) and approx. 1.2 g of ethylenediaminetetraacetic acid (EDTA, >99.9%, from Aldrich) with approx. 17 ml of hot water. The material thus obtained was heated to 120° C. in a drying cabinet and dried overnight. Then approx. 1.2 g of iron(III) nitrate nonahydrate (>99%, from Riedel-de Haën) were dissolved in a further approx. 17 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 25

6% by Weight of Mo/1% by Weight of Ni on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to H, using 50 g of zeolite, approx. 5.9 g of the molybdate compound, 2.7 g of nickel(II) nitrate hexahydrate (>99%, from Riedel-de Haën) and approx. 4.1 g of ethylenediaminetetraacetic acid (EDTA, >99.9%, from Aldrich) with approx. 17 ml of hot water. The catalyst was tested according to G.

EXAMPLE 26

6% by Weight of Mo/0.5% by Weight of Fe on H-ZSM-5 (Spall) (Inventive)

A commercial H-ZSM-5 (ZEOcat PZ-2/25-H, from ZEOCHEM, $SiO_2:Al_2O_3$=approx. 25 mol/mol) support was pretreated according to A and then shaped to spall according to B. The catalyst was prepared from the spall thus obtained according to D. This involved impregnating approx. 15 g of the spall with approx. 1.8 g of ammonium heptamolybdate tetrahydrate (>99% from Aldrich) in approx. 17 ml of water. The material thus obtained was heated to 120° C. in a drying cabinet and dried overnight. Then approx. 0.6 g of iron(III) nitrate nonahydrate (>99%, from Riedel-de Haën) was dissolved in a further approx. 17 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 27

6% by Weight of Mo/1% by Weight of Cr on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to D, using 15 g of zeolite, approx. 1.8 g of the molybdate compound with approx. 17 ml of water. The material was heated to 120° C. in a drying cabinet and dried overnight. Then approx. 1.3 g of chromium(III) nitrate nonahydrate (>99%, from Riedel-de Haën) were dissolved in a further approx. 17 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 28

6% by Weight of Mo/1% by Weight of Ni/0.5% by Weight of Fe on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to I, initially using 15 g of zeolite, approx. 1.8 g of the molybdate compound, 0.8 g of nickel(II) nitrate hexahydrate (>99%, from Riedel-de Haën) and approx. 1.2 g of ethylenediaminetetraacetic acid (EDTA, >99.9%, from Aldrich) with approx. 17 ml of hot water. The material thus obtained was heated to 120° C. in a drying cabinet and dried overnight. Then approx. 0.6 g of iron(III) nitrate nonahydrate (>99%, from Riedel-de Haën) was dissolved in a further approx. 17 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 29

6% by Weight of Mo/1% by Weight of Ni/1% by Weight of Fe on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to I, initially using 15 g of zeolite, approx. 1.8 g of the molybdate compound, 0.8 g of nickel(II) nitrate hexahydrate (>99%, from Riedel-de Haën) and approx. 1.2 g of ethylenediaminetetraacetic acid (EDTA, >99.9%, from Aldrich) with approx. 17 ml of hot water. The material thus obtained was heated to 120° C. in a drying cabinet and dried overnight. Then approx. 1.2 g of iron(III) nitrate nonahydrate (>99%, from Riedel-de Haën) were dissolved in a further approx. 17 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 30

6% by Weight of Mo/1% by Weight of Ni/1% by Weight of Cr on H-ZSM-5 (Spall, EDTA) (Inventive)

A commercial H-ZSM-5 (ZEOcat PZ-2/25-H, from ZEOCHEM, $SiO_2:Al_2O_3$=approx. 25 mol/mol) support was pretreated according to A and B. The catalyst was prepared from the spall thus obtained according to I, initially using 15 g of zeolite, approx. 1.8 g of the molybdate compound, 0.8 g of nickel(II) nitrate hexahydrate (>99%, from Riedel-de Haën) and approx. 1.2 g of ethylenediaminetetraacetic acid (EDTA, >99.9%, from Aldrich) with approx. 17 ml of hot water. The material thus obtained was heated to 120° C. in a drying cabinet and dried overnight. Then approx. 1.3 g of chromium(III) nitrate nonahydrate (>99%, from Riedel-de Haën) were dissolved in a further approx. 17 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 31

6% by Weight of Mo/1% by Weight of Cu/0.5% by Weight of Nb on H-ZSM-5 (Spall, EDTA) (Inventive)

A commercial H-ZSM-5 (ZEOcat H-ZSM-5 PZ-2/25-H, from ZEOCHEM, $SiO_2:Al_2O_3$=approx. 25 mol/mol) support was pretreated according to A and B. The catalyst was prepared from the spall thus obtained according to I, initially using 15 g of zeolite, approx. 1.8 g of the molybdate compound, 0.6 g of copper(II) nitrate pentahemihydrate (>99%, from Riedel-de Haën) and approx. 1.2 g of ethylenediaminetetraacetic acid (EDTA, >99.9%, from Aldrich) with approx. 17 ml of hot water. The hot solution was added to the zeolite with stirring and the material was mixed further at room temperature for 15 min. The material thus obtained was heated to 120° C. in a drying cabinet and dried overnight. Then approx. 0.3 g of ammonium niobate(V)oxalate (>99%, from Aldrich) was dissolved in a further approx. 13 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

TABLE 7

Catalytic performance of the catalysts from Examples 19 to 31 after a reaction time of 10 h (zeolite: H-ZSM-5 with $SiO_2:Al_2O_3$ = approx. 25:1)

| Catalyst examples | Catalytically active metals | Preparation | Methane conversion [%] | Benzene selectivity [%] | Naphthalene selectivity [%] | Benzene yield [%] |
|---|---|---|---|---|---|---|
| 19 | 6% by weight Mo | A, B, C | 7.5 | 60.9 | 2.5 | 4.6 |
| 20 | 6% by weight Mo, 1% by weight Fe | A, B, D | 9.3 | 61.0 | 1.2 | 5.7 |

TABLE 7-continued

Catalytic performance of the catalysts from Examples 19 to 31 after a
reaction time of 10 h (zeolite: H-ZSM-5 with $SiO_2:Al_2O_3$ = approx. 25:1)

| Catalyst examples | Catalytically active metals | Preparation | Methane conversion [%] | Benzene selectivity [%] | Naphthalene selectivity [%] | Benzene yield [%] |
|---|---|---|---|---|---|---|
| 21 | 6% by weight Mo, 1% by weight Cu | A, B, F | 8.0 | 69.2 | 6.5 | 5.5 |
| 22 | 6% by weight Mo, 1% by weight Cu | A, B, H (EDTA) | 8.8 | 67.1 | 8.9 | 5.9 |
| 23 | 6% by weight Mo, 1% by weight Cu | A, B, H ($NH_3$) | 9.0 | 67.3 | 3.0 | 6.1 |
| 24 | 6% by weight Mo, 1% by weight Cu, 1% by weight Fe | A, B, I (EDTA) | 9.8 | 66.0 | 4.3 | 6.4 |
| 25 | 6% by weight Mo, 1% by weight Ni | A, B, H (EDTA) | 9.1 | 67.0 | 6.4 | 6.1 |
| 26 | 6% by weight Mo, 0.5% by weight Fe | A, B, D | 8.8 | 67.3 | 5.4 | 5.9 |
| 27 | 6% by weight Mo, 1% by weight Cr | A, B, D | 9.0 | 62.1 | 0.5 | 5.6 |
| 28 | 6% by weight Mo, 1% by weight Ni, 0.5% by weight Fe | A, B, I (EDTA) | 9.8 | 67.0 | 5.4 | 6.6 |
| 29 | 6% by weight Mo, 1% by weight Ni, 1% by weight Fe | A, B, I (EDTA) | 10.5 | 67.0 | 5.4 | 7.0 |
| 30 | 6% by weight Mo, 1% by weight Ni, 1% by weight Cr | A, B, I (EDTA) | 9.3 | 68.3 | 7.2 | 6.4 |
| 31 | 6% by weight Mo, 1% by weight Cu, 0.5% by weight Nb | A, B, I | 9.9 | 74 | 6.8 | 7.3 |

Naphthalene selectivity: proportion of naphthalene, based on methane converted, in percent
Benzene yield: proportion of benzene, based on methane used The presence of a complexing agent in the impregnation of the zeolite pretreated according to A and B with the catalytically active metals (examples 22 and 23) brings about a further increase in the methane conversions and benzene yields, compared to the catalyst impregnated with the metals without complexing agent (example 21). This is confirmed by the results shown in table 6.

These examples show a clear increase in the benzene selectivities and benzene yields in the presence of at least one further metal in the catalyst as well as Mo. The presence of two further elements as well as Mo in the catalyst brings about a clear increase in the benzene yield compared to the catalysts comprising only one of the further elements.

EXAMPLE 32

6% by Weight of Mo/1% by Weight of Ni/0.5% by Weight of Nb on H-ZSM-5 (Spall, EDTA) (Inventive)

A commercial H-ZSM-5 (ZEOcat PZ-2/25-H, from ZEOCHEM, $SiO_2:Al_2O_3$=approx. 50 mol/mol) support was pretreated according to A and B. The catalyst was prepared from the spall thus obtained according to I, initially using 15 g of zeolite, approx. 1.8 g of the molybdate compound, 0.8 g of nickel(II) nitrate hexahydrate (>99%, from Riedel-de Haën) and approx. 1.2 g of ethylenediaminetetraacetic acid (EDTA, >99.9%, from Aldrich) with approx. 10 ml of hot water. The hot solution was added to the zeolite with stirring and the material was mixed further at room temperature for 15 min. The material thus obtained was heated to 120° C. in a drying cabinet and dried overnight. Then approx. 0.3 g of ammonium(V) niobate oxalate (>99%, from Aldrich) was dissolved in a further approx. 13 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 33

6% by Weight of Mo/1% by Weight of Cu/0.5% by Weight of Nb on H-ZSM-5 (Spall, EDTA) (Inventive)

A commercial H-ZSM-5 (ZEOcat PZ-2/25-H, from ZEOCHEM, $SiO_2:Al_2O_3$=approx. 50 mol/mol) support was pretreated according to A and B. The catalyst was prepared from the spall thus obtained according to I, initially using 15 g of zeolite, approx. 1.8 g of the molybdate compound, 0.6 g of copper(II) nitrate pentahemihydrate (>99%, from Riedel-de Haën) and approx. 1.2 g of ethylenediaminetetraacetic acid (EDTA, >99.9%, from Aldrich) with approx. 17 ml of hot water. The hot solution was added to the zeolite with stirring and the material was mixed further at room temperature for 15 min. The material thus obtained was heated to 120° C. in a drying cabinet and dried overnight. Then approx. 0.3 g of ammonium(V) niobate oxalate (>99%, from Aldrich) was dissolved in a further approx. 13 ml of water, the solution was subsequently added to the zeolite with stirring and the material was mixed further at room temperature for 15 min. The material was heated to 120° C. in a drying cabinet, dried overnight and then calcined at 500° C. for 4 h. The catalyst was tested according to G.

EXAMPLE 34

6% by Weight of Mo/1% by Weight of Ni/0.5% by Weight of Ta on H-ZSM-5 (Spall, EDTA) (Inventive)

A commercial H-ZSM-5 (ZEOcat PZ-2/25-H, from ZEOCHEM, $SiO_2:Al_2O_3$=approx. 50 mol/mol) support was pretreated according to A and B. 15 g of the spall thus obtained were initially mixed dry with approx. 0.1 g tantalum (IV) carbide (from Aldrich). The catalyst was prepared from the mixture of spall and tantalum(IV) carbide according to I, using approx. 1.8 g of the molybdate compound, 0.8 g of nickel(II) nitrate hexahydrate (>99%, from Riedel-de Haën) and approx. 1.2 g of ethylenediaminetetraacetic acid (EDTA, >99.9%, from Aldrich) with approx. 10 ml of hot water. The hot solution was added to the zeolite with stirring and the material was mixed further at room temperature for 15 min. The material thus obtained was heated to 120° C. in a drying cabinet, dried overnight and then calcined at 500° C. for 4 h. The catalyst was tested according to G.

TABLE 8

Catalytic performance of the catalysts from Examples 32 to 34 after a reaction time of 10 h (zeolite: H-ZSM-5 with $SiO_2:Al_2O_3$ = approx. 50:1)

| Catalyst examples | Catalytically active metals | Preparation | Methane conversion [%] | Benzene selectivity [%] | Naphthalene selectivity [%] | Benzene yield [%] |
|---|---|---|---|---|---|---|
| 32 | 6% by weight Mo, 1% by weight Ni, 0.5% by weight Nb | A, B, I | 10.7 | 71 | 8.5 | 7.6 |
| 33 | 6% by weight Mo, 1% by weight Cu, 0.5% by weight Nb | A, B, I | 9.6 | 73 | 8.8 | 7.6 |
| 34 | 6% by weight Mo, 1% by weight Ni, 0.5% by weight Ta | A, B, I | 10.5 | 71 | 7.9 | 7.5 |

The addition of Nb or Ta to an Ni- and Mo-containing inventive catalyst achieves improved benzene yields, as does the addition of Nb to a Cu- and Mo-containing inventive catalyst.

EXAMPLE 35

Catalytic Test with Hydrogen Regeneration

Approx. 1.6 g of the catalyst from Example 32 are first tested in the reaction tube (internal diameter=4 mm) for 6 h according to G. After approx. 6 h, the reaction tube is inertized with helium and the temperature is raised to 740° C. and the pressure to p(tot.)=5 bar. This is followed by regeneration with pure $H_2$ for 4 h, restoring temperature and pressure to 700° C. and 1 bar under helium, and then starting a further reaction cycle of 6 h (T=700° C., p(tot.)=1 bar, approx. 90% by volume of $CH_4$, approx. 10% by volume of He, GHSV=500 $h^{-1}$). This procedure was repeated several times. The results are summarized in Table 9. The values reported refer in each case to the time 6 h after the start of the cycle.

TABLE 9

Regeneratability with hydrogen: catalytic performance of the catalyst from example 35 after a reaction time of 6 h in each case

|  | $CH_4$ conversion | Benzene selectivity |
| --- | --- | --- |
| $1^{st}$ cycle | 10.2% | 73% |
| $2^{nd}$ cycle | 10.3% | 73% |
| $3^{rd}$ cycle | 9.8% | 72% |
| $4^{th}$ cycle | 9.7% | 72% |
| $5^{th}$ cycle | 9.8% | 72% |

The invention claimed is:

1. A calcined MFI or MWW zeolite catalyst which comprises molybdenum and at least two elements selected from the group consisting of Cu, Ni, Fe, Co, Mn, Cr, Nb, Ta, Zr, V, Zn, and Ga.

2. The catalyst of claim 1, which is prepared by a process comprising:
 (I) treating a MFI or MWW zeolite with a mixture comprising at least one ammonium salt selected from the group consisting of ammonium carbonate, ammonium hydrogencarbonate, ammonium nitrate, ammonium acetate, ammonium phosphate, ammonium hydrogenphosphate, ammonium dihydrogenphosphate, ammonium sulfate, and ammonium hydrogensulfate, and subsequently drying and calcining the zeolite, to produce a primary zeolite;
 (II) treating the primary zeolite with a mixture comprising at least one ammonium salt selected from the group of ammonium carbonate, ammonium hydrogencarbonate, ammonium nitrate, ammonium acetate, ammonium phosphate, ammonium hydrogenphosphate, ammonium dihydrogenphosphate, ammonium sulfate, and ammonium hydrogensulfate, and subsequently drying the zeolite, to produce a secondary zeolite;
 (III) applying the molybdenum and at least two elements selected from the group consisting of Cu, Ni, Fe, Co, Mn, Cr, Nb, Ta, Zr, V, Zn, and Ga, to the secondary zeolite, to produce a catalyst precursor; and
 (IV) calcining the catalyst precursor.

3. The catalyst of claim 2, wherein the molybdenum and at least two elements selected from the group consisting of Cu, Ni, Fe, Co, Mn, Cr, Nb, Ta, Zr, V, Zn, and Ga are applied to the secondary zeolite in the form of a solution, and wherein the solution further comprises a complexing agent.

4. The catalyst of claim 2, wherein the at least one ammonium salt in (I) and (II) is ammonium nitrate.

5. The catalyst of claim 2, which is obtained by mixing the zeolite with an Si-comprising binder between (I) and (II), or (II) and (III).

6. The catalyst of claim 1, which comprises from 0.1 to 20% by weight, based on a total weight of the catalyst, of Mo.

7. The catalyst of claim 1, which comprises at least 0.1% by weight, based on a total weight of the catalyst, of the at least two elements selected from the group consisting of Cu, Ni, Fe, Co, Mn, Cr, Nb, Ta, Zr, V, Zn, and Ga.

8. The catalyst of claim 1, which comprises at least 0.1% by weight of at least one first element selected from the group consisting of Mn, Cr, Nb, Ta, Zr, V, Zn, Ga, Cu, Ni, Fe, and Co, and at least 0.05% by weight of the at least one second element selected from the group consisting of Cu, Ni, Fe, Co, Cr, Zr, V, Zn, and Ga, based in each case on a total weight of the catalyst.

9. The catalyst of claim 1, in the form of spall or shaped bodies.

10. The catalyst of claim 1, in the form of a powder.

11. The catalyst of claim 1, which comprises at least one element selected from the group consisting of Cu, Ni, Fe, Nb, Ta and Co.

12. The catalyst of claim 1, which comprises at least one element selected from the group consisting of Cu, Ni and Fe.

13. A calcined MFI or MWW zeolite catalyst which comprises molybdenum and at least one element selected from the group consisting of Cu, Ni, Fe, Co, Mn, Cr, Nb, Ta, Zr, V, Zn, and Ga, prepared by a process comprising:
 (I) treating a MFI or MWW zeolite with a mixture comprising at least one ammonium salt selected from the group consisting of ammonium carbonate, ammonium hydrogencarbonate, ammonium nitrate, ammonium acetate, ammonium phosphate, ammonium hydrogenphosphate, ammonium dihydrogenphosphate, ammonium sulfate, and ammonium hydrogensulfate, and subsequently drying and calcining the zeolite, to produce a primary zeolite;
 (II) treating the primary zeolite with a mixture comprising at least one ammonium salt selected from the group of ammonium carbonate, ammonium hydrogencarbonate, ammonium nitrate, ammonium acetate, ammonium phosphate, ammonium hydrogenphosphate, ammonium dihydrogenphosphate, ammonium sulfate, and ammonium hydrogensulfate, and subsequently drying the zeolite, to produce a secondary zeolite;
 (III) applying a solution comprising molybdenum, at least one element selected from the group consisting of Cu, Ni, Fe, Co, Mn, Cr, Nb, Ta, Zr, V, Zn, and Ga, and a complexing agent, to the secondary zeolite, to produce a catalyst precursor; and
 (IV) calcining the catalyst precursor.

14. The catalyst of claim 13, wherein the at least one ammonium salt in (I) and (II) is ammonium nitrate.

15. The catalyst of claim 13, which comprises from 0.1 to 20% by weight, based on a total weight of the catalyst, of Mo.

16. The catalyst of claim 13, which comprises at least 0.1% by weight, based on a total weight of the catalyst, of the at least one further element selected from the group consisting of Cu, Ni, Fe, Co, Mn, Cr, Nb, Ta, Zr, V, Zn, and Ga.

17. The catalyst of claim 13, which comprises at least 0.1% by weight of the at least one element selected from the group consisting of Mn, Cr, Nb, Ta, Zr, V, Zn, Ga, Cu, Ni, Fe, and Co, and at least 0.05% by weight of the at least other element selected from the group consisting of Cu, Ni, Fe, Co, Cr, Zr, V, Zn, and Ga, based in each case on a total weight of the catalyst.

18. The catalyst of claim 13, which is obtained by mixing the zeolite with an Si-comprising binder between (I) and (II), or (II) and (III).

19. The catalyst of claim 13, in the form of spall or shaped bodies.

20. The catalyst of claim 13, in the form of a powder.

21. The catalyst of claim 13, which comprises at least two elements selected from the group consisting of Mn, Cr, Nb, Ta, Zr, V, Zn, Ga, Cu, Ni, Fe, and Co.

22. The catalyst of claim 13, which comprises at least one element selected from the group consisting of Cu, Ni, Fe, Nb, Ta and Co.

23. The catalyst of claim 13, which comprises at least one element selected from the group consisting of Cu, Ni and Fe.

24. A method of preparing the catalyst of claim 1, comprising:
(I) treating a MFI or MWW zeolite with a mixture comprising at least one ammonium salt selected from the group consisting of ammonium carbonate, ammonium hydrogencarbonate, ammonium nitrate, ammonium acetate, ammonium phosphate, ammonium hydrogenphosphate, ammonium dihydrogenphosphate, ammonium sulfate, and ammonium hydrogensulfate, and subsequently drying and calcining the zeolite, to produce a primary zeolite;
(II) treating the primary zeolite with a mixture comprising at least one ammonium salt selected from the group of ammonium carbonate, ammonium hydrogencarbonate, ammonium nitrate, ammonium acetate, ammonium phosphate, ammonium hydrogenphosphate, ammonium dihydrogenphosphate, ammonium sulfate, and ammonium hydrogensulfate, and subsequently drying the zeolite, to produce a secondary zeolite;
(III) applying the molybdenum and at least two elements selected from the group consisting of Cu, Ni, Fe, Co, Mn, Cr, Nb, Ta, Zr, V, Zn, and Ga, to the secondary zeolite, to produce a catalyst precursor; and
(IV) calcining the catalyst precursor.

25. A method of preparing the catalyst of claim 13, comprising:
(I) treating a MFI or MWW zeolite with a mixture comprising at least one ammonium salt selected from the group consisting of ammonium carbonate, ammonium hydrogencarbonate, ammonium nitrate, ammonium acetate, ammonium phosphate, ammonium hydrogenphosphate, ammonium dihydrogenphosphate, ammonium sulfate, and ammonium hydrogensulfate, and subsequently drying and calcining the zeolite, to produce a primary zeolite;
(II) treating the primary zeolite with a mixture comprising at least one ammonium salt selected from the group of ammonium carbonate, ammonium hydrogencarbonate, ammonium nitrate, ammonium acetate, ammonium phosphate, ammonium hydrogenphosphate, ammonium dihydrogenphosphate, ammonium sulfate, and ammonium hydrogensulfate, and subsequently drying the zeolite, to produce a secondary zeolite;
(III) applying a solution comprising molybdenum, at least one element selected from the group consisting of Cu, Ni, Fe, Co, Mn, Cr, Nb, Ta, Zr, V, Zn, and Ga, and a complexing agent, to the secondary zeolite, to produce a catalyst precursor; and
(IV) calcining the catalyst precursor.

26. A method of dehydroaromatizing a reactant stream, comprising contacting a reactant stream comprising $C_1$-$C_4$-aliphatics with the catalyst of claim 1.

27. A method of dehydroaromatizing a reactant stream, comprising contacting a reactant stream comprising $C_1$-$C_4$-aliphatics with the catalyst of claim 13.

* * * * *